United States Patent
West

(10) Patent No.: US 10,036,063 B2
(45) Date of Patent: Jul. 31, 2018

(54) METHOD FOR SEQUENCING A POLYNUCLEOTIDE TEMPLATE

(75) Inventor: John Stephen West, Cupertino, CA (US)

(73) Assignee: ILLUMINA, INC., San Diego, CA (US)

(*) Notice: Subject to any disclaimer, the term of this patent is extended or adjusted under 35 U.S.C. 154(b) by 414 days.

(21) Appl. No.: 13/384,302

(22) PCT Filed: Jun. 30, 2010

(86) PCT No.: PCT/US2010/040568
§ 371 (c)(1),
(2), (4) Date: Mar. 12, 2012

(87) PCT Pub. No.: WO2011/011175
PCT Pub. Date: Jan. 27, 2011

(65) Prior Publication Data
US 2012/0165205 A1    Jun. 28, 2012

Related U.S. Application Data

(60) Provisional application No. 61/267,561, filed on Dec. 8, 2009, provisional application No. 61/228,413, filed on Jul. 24, 2009.

(51) Int. Cl.
| C12Q 1/68 | (2018.01) |
| C07H 21/02 | (2006.01) |
| C07H 21/04 | (2006.01) |
| C12Q 1/6869 | (2018.01) |

(52) U.S. Cl.
CPC .................. *C12Q 1/6869* (2013.01)

(58) Field of Classification Search
None
See application file for complete search history.

(56) References Cited

U.S. PATENT DOCUMENTS

| 5,302,509 | A | 4/1994 | Cheeseman |
| 5,714,330 | A * | 2/1998 | Brenner et al. .............. 435/6.18 |
| 5,750,341 | A | 5/1998 | Macevicz |
| 5,763,594 | A | 6/1998 | Hiatt et al. |
| 5,808,045 | A | 9/1998 | Hiatt et al. |
| 5,872,244 | A | 2/1999 | Hiatt et al. |
| 6,232,465 | B1 | 5/2001 | Hiatt et al. |
| 6,306,597 | B1 | 10/2001 | Macevicz |
| 6,613,513 | B1 * | 9/2003 | Parce et al. .......... C12Q 1/6874 435/6.11 |
| 7,056,706 | B2 | 6/2006 | Senapathy |
| 7,057,026 | B2 | 6/2006 | Barnes et al. |
| 7,115,400 | B1 | 10/2006 | Adessi et al. |
| 7,169,557 | B2 * | 1/2007 | Rosenblum et al. ........ 435/6.14 |
| 7,198,893 | B1 * | 4/2007 | Koster et al. ........ B01J 19/0046 435/6.16 |
| 7,323,305 | B2 | 1/2008 | Leamon et al. |
| 7,329,860 | B2 | 2/2008 | Feng et al. |
| 7,541,444 | B2 | 6/2009 | Milton et al. |
| 8,236,532 | B2 | 8/2012 | Ronaghi et al. |
| 2004/0106110 | A1 | 6/2004 | Balasubramanian et al. |
| 2005/0042649 | A1 | 2/2005 | Balasubramanian et al. |
| 2005/0100900 | A1 | 5/2005 | Kawashima et al. |
| 2006/0134633 | A1 | 6/2006 | Chen et al. |
| 2007/0002890 | A1 | 1/2007 | Mangold et al. |
| 2007/0010251 | A1 | 1/2007 | Cho et al. |
| 2007/0026438 | A1 | 2/2007 | Smith et al. |
| 2007/0128624 | A1 | 6/2007 | Gormley et al. |
| 2007/0141604 | A1 | 6/2007 | Gormley et al. |
| 2007/0243535 | A1 | 10/2007 | Harris |
| 2008/0003571 | A1 | 1/2008 | McKernan et al. |
| 2008/0051294 | A1 | 2/2008 | Gormley et al. |
| 2009/0088327 | A1 | 4/2009 | Rigatti et al. |
| 2009/0118128 | A1 | 5/2009 | Liu et al. |
| 2009/0181370 | A1 | 7/2009 | Smith |

FOREIGN PATENT DOCUMENTS

| GB | 2398383 | 8/2004 |
| WO | 1996/007669 | 3/1996 |
| WO | 98/44151 | 10/1998 |

(Continued)

OTHER PUBLICATIONS

Sommer and Tautz, "Minimal homology requirements for PCR primers," Nucleic Acids Research, vol. 17, No. 16, 1989, p. 6749.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011 ).*
"Murinae," (Wikipedia.com, accessed Mar. 18, 2013).*
"Fish," (Wikipedia.com, accessed Nov. 2, 2014).*

(Continued)

*Primary Examiner* — Bradley L. Sisson
(74) *Attorney, Agent, or Firm* — Mueting, Raasch & Gebhart, P.A.

(57) ABSTRACT

A method of determining the sequence of a target nucleic acid is provided. The method can include the steps of (a) performing a defined number of incremental extension cycles to produce a population of nucleic acid fragments having different portions of the target nucleic acid wherein the individual nucleic acid fragments in the population have a defined length that is correlated with the number of incremental extension cycles; (b) determining the sequence of the first end of individual nucleic acid fragments in the population, thereby providing first end sequences; (c) determining the sequence of the second end of individual nucleic acid fragments in the population, thereby providing second end sequences; and (d) determining the sequence of the target nucleic acid based on the first end sequences, the second end sequences and the defined length.

15 Claims, 1 Drawing Sheet

(56) References Cited

FOREIGN PATENT DOCUMENTS

| WO | 00/06770 | 2/2000 |
|---|---|---|
| WO | 2000/018957 | 4/2000 |
| WO | 2004/018497 | 3/2004 |
| WO | 2004/069849 | 8/2004 |
| WO | WO 2004/070005 A2 | 8/2004 |
| WO | WO 2005/039389 A2 | 5/2005 |
| WO | 2005/068656 | 7/2005 |
| WO | 2006/084132 | 8/2006 |
| WO | 2007/010252 | 1/2007 |
| WO | WO 2007/010263 A2 | 1/2007 |
| WO | 2007/052006 | 5/2007 |
| WO | 2007/057652 | 5/2007 |
| WO | WO 2007/075967 A2 | 7/2007 |
| WO | 07/091077 | 8/2007 |
| WO | WO 2007/091077 A1 | 8/2007 |
| WO | 2007/123744 | 11/2007 |
| WO | 2007/135368 | 11/2007 |
| WO | 2008/002502 | 1/2008 |
| WO | 2008/041002 | 4/2008 |
| WO | 2009/032167 | 3/2009 |
| WO | 2009032167 | 3/2009 |
| WO | WO 2009/051807 A1 | 4/2009 |
| WO | WO 2009/079488 A1 | 6/2009 |
| WO | 2009/097626 | 8/2009 |
| WO | 2010/127304 | 11/2010 |

OTHER PUBLICATIONS

"List of sequenced bacterial genomes" (Wikipedia.com; accessed Jan. 24, 2014).*

"Human Hybrids," by Michael F. Hammer, Scientific American, May 2013, pp. 66-71.*

Bentley et al., "Accurate whole human genome sequencing using reversible terminator chemistry", Nov. 6, 2008, Nature, 456:53-9.

Bentley et al., "Supplementary Information", www.nature.com/nature, doi:10.1038/nature07517.

Housby, "Optimised ligation of oligonucleotides by thermal ligases: comparison of *Thermus scotoductus* and *Rhodothermus marinus* DNA ligases to other thermophilic liagses", 2000, *Nucleic Acids Research*, 28(3):e10, pp. i-v.

Metzker, "Emerging technologies in DNA sequencing", 2005, *Genome Research*, 15:1767-76.

Mir et al., "Sequencing by Cyclic Ligation and Cleavage (CycLiC) directly on microarray captured template", Nov. 16, 2008, *Nucleic Acids Research*, 37(1): e5, pp. 1-8.

Notice of Opposition, "EP Application No. 10802636.0", dated Jun. 26, 2015.

Ronaghi et al., "Real-Time DNA Sequencing Using Detection of Pyrophosphate Release", May 6, 1996, *Analytical Biochemistry*, 242:84-9.

* cited by examiner

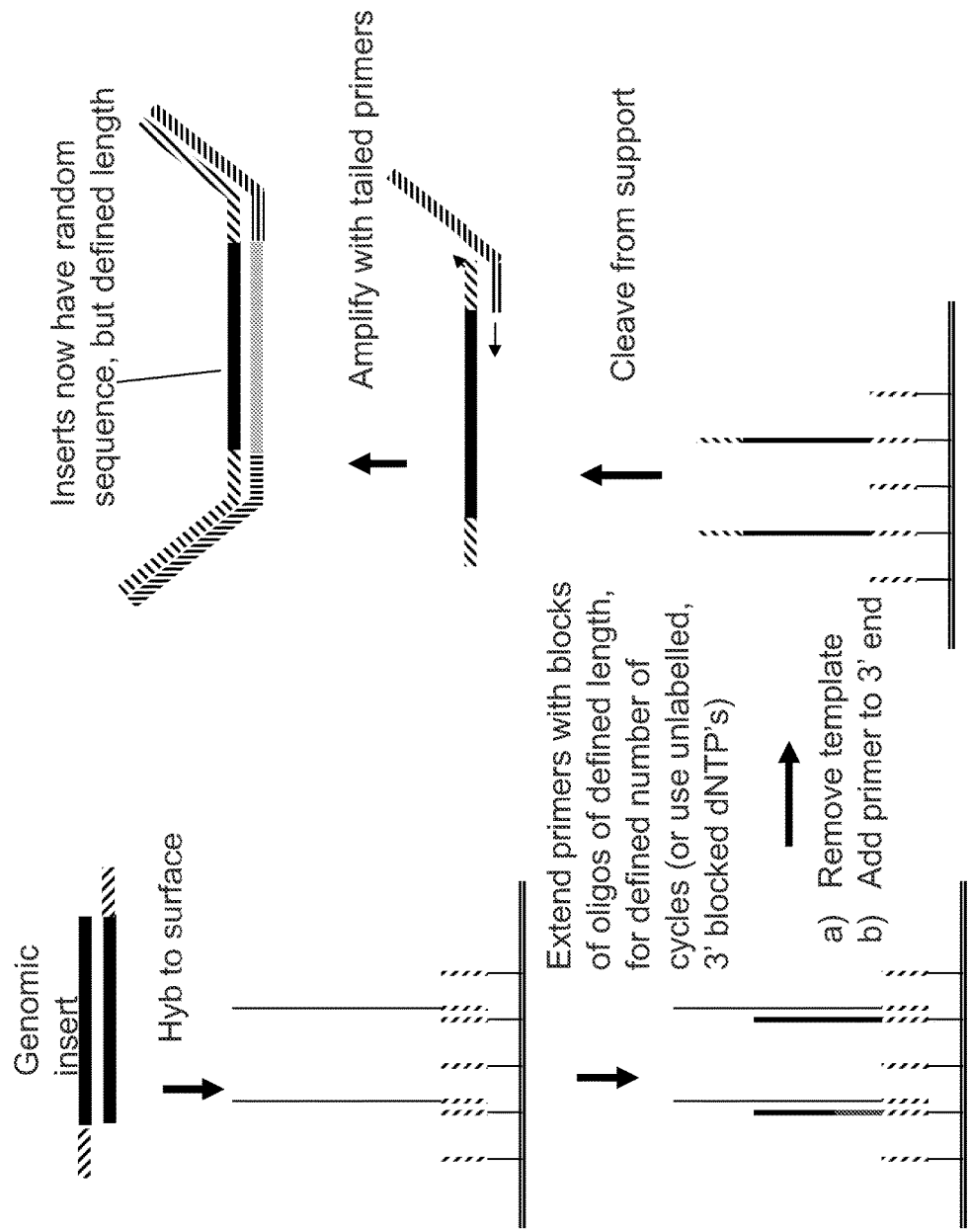

METHOD FOR SEQUENCING A POLYNUCLEOTIDE TEMPLATE

REFERENCE TO RELATED APPLICATIONS

This application claims priority to U.S. Provisional Application Ser. Nos. 61/228,413 filed on Jul. 24, 2009, and 61/267,561 filed on Dec. 8, 2009, which are incorporated herein by reference in their entireties.

FIELD OF THE INVENTION

The invention relates to the field of nucleic acid sequence analysis. More specifically, the invention relates to methods for pairwise sequencing of a double-stranded polynucleotide template, which methods result in the sequential determination of nucleotide sequences in two distinct and separate regions of the polynucleotide template.

BACKGROUND TO THE INVENTION

Advances in the study of biological molecules have been led, in part, by improvement in technologies used to characterise the molecules or their biological reactions. In particular, the study of the nucleic acids DNA and RNA has benefited from developing technologies used for sequence analysis.

Methods for sequencing a polynucleotide template can involve performing multiple extension reactions using a DNA polymerase or DNA ligase, respectively, to successively incorporate labelled nucleotides or polynucleotides complementary to a template strand. In such "sequencing by synthesis" reactions a new nucleotide strand base-paired to the template strand is built up by successive incorporation of nucleotides complementary to the template strand. The substrate nucleoside triphosphates or oligonucleotides used in the sequencing reaction are typically blocked to prevent over-incorporation. The substrate nucleoside triphosphates or oligonucleotides can also be labelled, permitting determination of the identity of the incorporated nucleotide(s) as successive nucleotides are added.

In order to carry out accurate sequencing using nucleoside triphosphates, a reversible chain-terminating structural modification or "blocking moiety" may be added to the substrate nucleotides to ensure that nucleotides are incorporated one at a time in a controlled manner. As each single nucleotide is incorporated, the blocking moiety prevents any further nucleotide incorporation into the polynucleotide chain. Once the identity of the last-incorporated labelled nucleotide has been determined the label moiety and blocking moiety are removed, allowing the next blocked, labelled nucleotide to be incorporated in a subsequent round of sequencing.

In certain circumstances the amount of sequence data that can be reliably obtained with the use of sequencing-by-synthesis techniques, particularly when using blocked, labelled nucleotides, may be limited. In some circumstances the sequencing "run" may be limited to a number of bases that permits sequence realignment with the human genome, for example around 50-100 cycles of incorporation. Whilst sequencing runs of this length are extremely useful, particularly in applications such as, for example, SNP analysis and genotyping, it would be advantageous in many circumstances to be able to reliably obtain further sequence data for the same template molecule.

The technique of "paired-end" or "pairwise" sequencing is generally known in the art of molecular biology, particularly in the context of whole-genomic shotgun sequencing. Many applications in DNA sequencing use paired-end methods to obtain sequence information on a length scale longer than an individual read. Paired-end sequencing allows the determination of two "reads" of sequence from two places on a single polynucleotide duplex. The advantage of the paired-end approach is that there is significantly more information to be gained from sequencing two stretches each of "n" bases from a single template than from sequencing "n" bases from each of two independent templates in a random fashion. With the use of appropriate software tools for the assembly of sequence information it is possible to make use of the knowledge that the "paired-end" sequences are not completely random, but are known to occur on a single duplex, and are therefore linked or paired in the genome. This information has been shown to greatly aid the assembly of whole genome sequences into a consensus sequence. It is especially advantageous for the alignment and assembly of the genome sequences if each of the fragments is of a defined known length such that the distance between the two reads is accurately defined and controlled.

Paired-end sequencing has typically been performed by making use of specialized circular shotgun cloning vectors known in the art. After cutting the vector at a specific single site, the template DNA to be sequenced (typically genomic DNA) is inserted into the vector and the ends resealed to form a new construct. The vector sequences flanking the insert DNA include binding sites for sequencing primers which permit sequencing of the insert DNA at each end and on opposite strands.

A disadvantage of this approach is that it requires time-consuming cloning of the DNA sequencing templates into an appropriate sequencing vector. Furthermore, there is little to no control of the length of the fragments inserted into the vector. Moreover, cloning the DNA template into a vector, although allowing binding sites for sequencing primers to be positioned at both ends of the template fragment, can be cumbersome and inefficient when used for array-based sequencing techniques. With array-based techniques a sequence is generally read from one end of a nucleotide template, this often being the end proximal to the point of attachment to the array. However, a variety of methods for double-ended sequencing of a polynucleotide template are known.

Also known are methods of nucleic acid amplification which generate amplification products immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions but only a single sequencing read is typically obtained from one type of immobilised strand in each colony.

An exemplary method that is useful for paired end sequencing on clusters uses three grafted primers. This method is applicable to templates that can be amplified using bridge amplification, and the length of the templates used may be up to, for example, 1000 base pairs or so, however for many DNA sequencing applications, it may be necessary to determine a sequence read from either end of a target fragment of greater length. The sample preparation methods described in the present invention allow the analysis of a pair of reads for the ends of a fragment of any length.

An alternative method for sequencing both ends of a cluster is the use of strand resynthesis. Once a first read is completed, the template can be copied using immobilised primers to generate a second template strand. The second template strand can be sequenced to give a second read. Thus the cluster is sequenced from both ends.

In preparing DNA for these applications, a narrow length distribution is desired because it offers increased bioinformatic power. In resequencing for example, if it is known that a fragment is N bases +/−M bases, then it is possible to detect insertions and deletions in the non-sequenced part of the fragment which are at least M bases. The smaller M can be, the more powerful the paired end data is. In the limit where M=0, i.e. where the fragment length is known exactly, it is possible to detect even single base insertions or deletions in the unread part of the fragment, by noting spacing of the reads when mapped to the reference that is not as expected. Single base insertions and deletions are common in the human genome and thus some of the most important to detect. By creating molecule sets which are exact in length, detection of single base insertions and deletions by paired-end sequencing becomes possible with much lower sequencing coverage and thus at much lower cost.

A standard method used to obtain a specific narrow fragment length distribution has two steps. The first step fragments the source target DNA (which is originally very long—e.g. Genomic DNA) into shorter pieces. Methods used include sonication, forcing through a nozzle that forms tiny droplets (nebulisation), heat and radiation. These methods typically result in random fragments (e.g. Minimal base-composition bias) but wide length distributions. The second step is to use a separation technique, e.g. Electrophoresis or HPLC, to resolve this size distribution so that a small fraction can be extracted that has a narrow size distribution. With manual electrophoresis, a slice or stab may be manually taken from a slab gel. With HPLC or automated capillary electrophoresis, an automated fraction collector could be used.

There are two problems with these approaches. First, the size selection process throws away most of the DNA (i.e. all the fragments which are the wrong length). This is a significant waste, particularly where the amount of source DNA can be very limited (e.g. as in a tumor biopsy). The narrower the size range selected, the lower the percentage utilization of the input DNA.

The second problem is that the narrowness of the size range is determined by the separation precision of the separation technique used. There are both theoretical limits to the precision and practical difficulties in achieving those theoretically possible levels. In any technique based on the separation of physical fragments it is very difficult to obtain a collection of fragments where each fragment is exactly the same length. The inventors herein have therefore developed a method of preparing fragments of defined length for the purposes of paired end sequencing.

SUMMARY OF THE INVENTION

The present invention provides, in particular embodiments, a method for preparing a nucleic acid sample such that it is suitable for paired-end, or pairwise sequencing. The method involves the preparation of fragments of a defined length wherein the length of each of the fragments is controlled by the use of incremental extension cycles and is substantially independent of the different sequences of the fragments.

Using a method of the invention it is possible to prepare a nucleic acid sample to obtain two linked or paired reads of sequence information from each of several double-stranded templates, wherein the gap between the two reads is of a defined length.

In accordance with the methods described herein a population of nucleic acid fragments for sequencing is generated synthetically using cycles of extension on each of several target nucleic acids. Use of a defined number of cycles, for example with blocked dNTPs or oligonucleotides, gives rise to a population of nucleic acid fragments having fragments of known length. Sequencing both ends of each fragment gives rise to a collection of nucleic acid sequence pairs where the distance between the two reads in each pair is known.

According to a first aspect of the invention there is provided a method of analysing a nucleic acid sample. The method can include the steps of (a) performing a defined number of incremental extension cycles to produce a population of nucleic acid fragments having different portions of the target nucleic acid wherein the individual nucleic acid fragments in the population have a defined length that is correlated with the number of incremental extension cycles; (b) determining the sequence of the first end of individual nucleic acid fragments in the population, thereby providing first end sequences; (c) determining the sequence of the second end of individual nucleic acid fragments in the population, thereby providing second end sequences; and (d) determining the sequence of the target nucleic acid based on the first end sequences, the second end sequences and the defined length.

According to a second aspect of the invention, there is provided a synthesised population of nucleic acid fragments including a collection of different nucleic acid fragments wherein each fragment has a universal 3' end and a universal 5' end, and wherein the length of each fragment in the population is controlled by the number of cycles of extension that was performed to synthesize the fragments such that the population has a defined length of between 200 to 1000 bases and at least 50% of the fragments vary in length by less than 5 nucleotides.

Other aspects of the invention cover the use of a population of nucleic acid fragments, for example, in sequencing, or in the formation of nucleic acid arrays for nucleic acid analysis.

BRIEF DESCRIPTION OF THE FIGURES

FIG. 1 shows a summary of the steps involved in one implementation of the method.

DETAILED DESCRIPTION OF THE INVENTION

The invention provides methods for preparing a nucleic acid sample for paired end sequencing. In one implementation of the method, each nucleic acid fragment in the sample is prepared using incremental extension cycles such that sequencing two regions of the target double-stranded polynucleotide template is possible, referred to herein as the first and second regions, wherein the distance between the first and second regions is defined by the number of extension cycles carried out.

The term "paired end sequencing" refers to a pair of reads obtained by sequencing two distinct regions, either on the same strand or the complementary strands of a particular target polynucleotide molecule. The paired end reads can be separated by a distance that is defined by the length of the nucleic acid strands. If the length of each sequencing read is more than half the length of the strands, then the pair of reads will fully sequence each base in the target polynucleotide molecule, and the bases in the centre of each strand will be read in both reads of the pair. Alternatively, the strands may be longer than twice the length of each read such that the central portion of the target polynucleotide molecule is not sequenced in either read. For example an individual strand may be 1000 bases in length, and each read may be 100 bases such that 100 bases at each end of the strand is known, and the sequence of the 800 bases in the centre of the strand is not determined. In particular embodiments, the paired end reads can cover at most 90%, 75%, 50%, 25%, 10%, 5% or 1% of the sequence present in each target polynucleotide molecule.

As used herein, the term "incremental extension cycle" means one or more steps that are carried out to add a single nucleotide or single oligonucleotide to a nucleic acid in a manner which prevents more than a single nucleotide or oligonucleotide from being added. For example, one or more steps can be carried out to add a single nucleotide to a primer nucleic acid using a polymerase. The nucleotide can have a reversible blocking moiety such that only a single nucleotide is added during each incremental extension cycle and removal of the blocking moiety allows subsequent extension to occur. Further by way of example, one or more steps can be carried out to add a single oligonucleotide to a primer nucleic acid using a ligase. The oligonucleotide can have a reversible blocking moiety at the 3' or 5' end such that only a single oligonucleotide is added during each incremental extension cycle and removal of the blocking moiety allows subsequent extension to occur. Exemplary steps that can be included in an incremental extension cycle include one or more of contacting a nucleic acid with a nucleotide or oligonucleotide; contacting a blocked nucleic acid with a deblocking agent to remove a blocking moiety from the 3' or 5' end; and washing a nucleic acid to remove unreacted reagents such as a nucleotide, oligonucleotide or deblocking agent.

In order to produce a strand complementary to a template, a priming sequence may be used. In cases where the sequence of the template is not known or where several different template sequences are present in a population, a region of known sequence can be introduced into the unknown sequence or into the different sequences in the population. The region of known sequence can be a "universal" priming site that is the same for different members of the population to which it was introduced and thus suitable for hybridising a known "universal" primer of a single sequence capable of hybridising to each member of the population. Alternatively a population of short oligonucleotides of random sequence can be used as primers. In either case, it is possible to hybridise primers without any knowledge of the template sequence. Some embodiments of the invention therefore utilize a single stranded template DNA and hybridise a primer to the template in a manner independent of the template sequences. This may be carried out by, for example, either using random primers or by ligation of an adapter sequence that serves as a universal priming site. The second strand may be extended from the primer by a known number of cycles of extension, for example using nucleotides with reversible blocking moieties. This will create a double stranded segment whose length is the length of the primer plus the number of bases added by synthesis using reversible blocking moieties. Alternatively the primer can be extended using randomised oligonucleotides (e.g. 10 mers where each of the possible 4^10 (1048576) different sequences is present). This will create a double stranded segment whose length is determined by the length of the primer plus the number of bases added, where the number of bases added is a product of the length of the oligonucleotide times the number of cycles of extension.

As used herein, the term "correlated," when used in reference to a defined length of a nucleic acid and a number of incremental extension cycles, means the defined length can be or is directly known from the number of incremental extension cycles. In particular embodiments, the correlation can allow for inefficiencies inherent in the extension methods used, for example, by including a measure of statistical confidence. In embodiments where a single nucleotide is added to a nucleic acid in each incremental extension cycle there can be a 1 to 1 correlation between the number of cycles and the defined length. In embodiments where an oligonucleotide of length N is added to a nucleic acid in each incremental extension cycle there can be a 1 to N correlation between the number of cycles and the defined length.

The length distribution created by either of these methods will be dependent on the chemical or enzymatic efficiency of the individual steps, namely the phasing & pre-phasing of the cycles of extension, and the number of those cycles. Phasing is a measure of the level of molecules which lag behind the correct length. A phasing level of 1% means that for 99 molecules which are extended in an extension cycle, 1 molecule fails to undergo extension and is therefore one base shorter than the other members of the population. Phasing may be caused by inefficiencies in extension or deblocking for example. Pre-phasing is a measure of the number of molecules which are longer than expected. Thus a pre-phasing of 1% means that for 99 molecules which are extend by a single base, one is extended by two bases. Pre-phasing may be caused by the addition of two monomers (nucleotides or oligonucleotides) in a single extension cycle. In the case of single nucleotide addition, phasing and pre-phasing contribute to providing a population of fragments where the length of every member of the population is not exactly the same as the number of incremental cycles performed. The length of each fragment in the population is therefore correlated with the number of incremental extension cycles, but each member may not be exactly the same length as the number of incremental extension cycles. Thus performing 200 cycles of extension will not necessarily give rise to a population of fragments where each fragment is exactly 200 bases in length. However the population will be tightly spread, and close to a length of 200 bases.

Fragments which are synthesised as complementary copies of a template do not typically result in consumption of the template strands from the target nucleic acid sample. Therefore the target sample is not typically lost or consumed by carrying out the methods described. In such embodiments, no separation technique is required in preparing the fragments, and hence there is no exclusion of fragments which are outside the desired length range. Therefore an advantage of the methods is that a particular source of inefficiency in the use of the original sample material can be eliminated. The length of the fragments is essentially known, and can be defined and controlled by a user.

For example, a user of a method set forth herein may be aiming for fragments of 500 bases in length. This may be obtained by 500 cycles of extension using single nucleotides, or 50 cycles of extension using 10-mer oligonucleotides. However, the inefficiencies in each process may be different. For single additions, the efficiencies will give rise to fragments that differ in length by single base increments, whereas for 10-mer oligonucleotides, the fragments which are not 500 bases in length will differ by multiples of 10 bases. In all cases, the aim of the method is to obtain as many fragments as possible of exactly the same length, even though not all fragments may be the same length unless the process of synthesising the strands is 100% efficient per cycle. One aspect of the invention is the use of incremental cycles of extension to synthesise fragment strands for subsequent paired end sequencing.

The length of the fragments is defined by the number of extension cycles performed. For an extension cycle that is 99.5% efficient per cycle, after 200 cycles 36% of the fragments will be exactly 200 bases in length, with the majority of the fragments varying in length by only a few bases. For example, at least 50% of the fragments generated in the whole collection may vary in size by less than 5 nucleotides such that at least 50% of the material is between 195-205 bases. A library generated in this manner can therefore comprise a much tighter distribution of sizes than can be obtained by physical separation of fragments. For example the population of fragments may be generated by carrying out 300 cycles of incremental extension such that at least 50% of the material is between 290-310 bases in length, or by carrying out 500 cycles of extension such that at least 50% of the material is greater than 480 bases in length. Typically, as more cycles of extension are carried out, the spread in the length of the members of the population increases. Accordingly in particular embodiments the spread can result in at least 50%, 60%, 70%, 80%, 90% or 95% of the fragments having a length that is the same as the number of extension cycles performed. The length of fragments produced by incremental extension cycles can be at least 100, 200, 300, 400, 500, 600, 700, 800, 900 or 1000 or more nucleotides in length.

Furthermore, when synthesizing long nucleic acid molecules by many cycles of synthesis chemistry in particular embodiments of the invention, the width of the fragment size distribution will be narrower than the phasing or pre-phasing percentage of each individual cycle. As a numerical example using single nucleotide additions per cycle, synthesizing a 1000 nucleotide fragment with 1% phasing would mean the average resulting molecule would have 990 nucleotides, i.e. that on average, each molecule would have suffered 10 single-base phasing events. If these are statistically independent, then they will have a Poisson distribution, with standard deviation approximately the square root of the number of events. Thus the size distribution would end up as 990+/−3.2 bases. This would be a standard deviation in fragment length of 0.32%, even though phasing was 1%. This is much narrower than can be achieved by typical electrophoretic or HPLC size selection methods. Further examples of the distribution of lengths of members of the population are for a 1% phasing over 300 cycles, 297 bases +/−1.7 bases or for 400 cycles at 0.5% phasing 398 bases +/−1.4 bases. Desirable phasing for various embodiments of the methods set forth herein can be at most about 0.1%, 0.25%, 0.5%, 1%, 2%, or 5%.

In order to further increase the accuracy regarding the lengths of the fragments obtained, an incremental extension process may be carried out more than once. By combining incremental extension methods one after the other, it is possible to create a library in which the fragment length distribution is tightly controlled, and therefore closer to length desired by the user when selecting the number of incremental extension cycles to perform. It may thus be possible to produce a population of fragments in which most or substantially all of the molecules are exactly the same length. In examples below, a representative length of 200 bases is chosen, but the numbers used in describing any embodiments of the invention are merely exemplary and should not be taken as limiting to the length of fragments obtainable using the methods described herein.

In a particular embodiment of the invention, the fragments may be synthesised to a user defined length, for example exactly 200 bases, by using a first set of extension cycles using addition of single nucleotides to the fragments, then a second set of extension cycles using ligation of oligonucleotides to the fragments. Upon synthesizing a certain length fragment, say 200 base pairs, using 200 single base additions, cycle inefficiencies will lead to a narrow distribution of molecules with lengths distributed close to the number of cycles performed, for example 198, 199, 200, 201 and 202 bases. Few molecules would be generated with lengths further away from the number of incremental cycles, for example 180, 190, 210, or 220 base lengths. On the other hand, if ligation is performed in 20 cycles each using a library of 10-mers, the aberrant lengths would be expected to be 180, 190, 210, or 220 bases (i.e. multiples of N bases away from the desired length for an N-mer library). Few of the molecules in the population would be closer to the desired length than N bases, for example in the 10-mer ligation set (N=10) few lengths would be 198, 199, 201 and 202 bases. When both of the above incremental extension techniques are carried out consecutively on the same original template, the only length at the intersection of the exemplary populations of product fragments should be exactly 200 bases, and hence most or substantially all of the fragments in the population should be the same number of bases in length. More specifically, first extension products which are shorter than 200 bases will not act as templates to produce full length second extension products of 200 base pairs, and first extension products longer than 200 bases will only act as templates for 20 cycles of 10-mer ligation, and hence the second extension products will terminate at exactly 200 bases. Only first extension products of exactly 200 bases will generate 200-base long double stranded DNA molecules with no residual single-stranded overhang during the second extension. Other length first extension products would have some single strand overhang, either in the first extension strand or the second extension strand.

In an alternative embodiment, a similar repetition of the incremental extension cycles to synthesise a second template strand can be carried out except that ligation extensions occur in both directions, but with different length N-mer libraries. For example templates can be synthesised first in one direction with 10-mers (N=10), and then the synthesized fragments can be used as templates for ligation-based synthesis in the other direction using 15-mers (N=15). As a result the lengths of the first and second strand duplexes can only match exactly every 150 bases. This could be used, for example, to synthesize a set of molecules which are an exact multiple of the lengths of the two different length N-mers. Any combination of length of oligonucleotides is suitable for use in the embodiment described herein, for example the oligonucleotides may be of any length. Oligonucleotides in libraries used for ligation-based extension may include randomised positions wherein two, three or four different bases are present at one or more of the positions in the oligonucleotides in the library. The oligonucleotides may be any of a variety of lengths including, for example, 2-20 bases in length.

If desired, single stranded overhanging regions that are present in fragments of undesired or otherwise aberrant lengths could serve as the basis for a pullout technique to remove them from the population. For example, oligonucleotides that have sequences that are complementary to the overhangs and that are immobilized to solid supports, such as beads, can be hybridized to unwanted fragments having the overhangs and then the solid supports that now carry the unwanted fragments can be removed from the desired fragments. Alternatively or additionally, the desired products obtained from two incremental extension cycles may be ligated to an adaptor which is blunt ended. Undesired fragments can be selectively removed based on the presence of single stranded overhangs that are incapable of undergoing ligation.

In a further embodiment, it may be possible to use a universal region at the end of the first extension products in order to selectively ligate to only the correct length products. After the required number of second incremental extension cycles, the ends of the second extension products may be ligated selectively to an oligonucleotide complementary to a universal sequence on the first extension products. In this case, only if the first extension product is joined to the universal region at the exact length of the second extension products will the second extension products undergo ligation to a sequence complementary to the universal region. For example if the first extension product is 198 bases followed by a universal region, a second template strand of 200 bases will not be able to ligate to a sequence complementary to the first universal region as the first two bases of the first universal region will already be hybridised to the longer second strand. Alternatively if the first extension product is 202 bases followed by a universal region, a second extension product of 200 base pairs will not undergo ligation to a sequence complementary to the universal region due to the two additional unpaired bases in the first extension strand. It is thus possible to produce templates of exactly 200 base pairs in length attached to a universal region at both ends.

Nucleic acid fragments can be synthesised using nucleotides carrying a reversible blocking moiety. A reversible blocking moiety can be located, for example, at the 3' position of the nucleotide. The blocking moiety may be a chemically cleavable moiety such as an allyl group, an azidomethyl group or a methoxymethyl group, or may be an enzymatically cleavable group such as a phosphate. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabelled. There is no need to record the identity of the bases as the fragments are prepared, so unlabelled nucleotides, which may give more efficient synthetic steps due the lack of modification on the nucleotide bases, can be used. Nucleotides used in a method set forth herein can be naturally occurring nucleotides lacking non-naturally occurring labels such as fluorescent moieties and other moieties used in analytical detection methods. Since there does not need to be a cleavable label, there does not need to be a pendant arm left on a nucleotide after each cycle of incorporation into a nucleic acid. Manufacture of nucleotides having blocking moieties and no fluorescent labels is typically less expensive than manufacture of nucleotides having blocking moieties and labels, both because they don't include expensive fluorescent dyes, and because typically fewer synthesis steps are needed, so yields are higher.

In a process of extending a second strand opposite a template strand, there is no need to observe the nucleotides incorporated at each cycle. Thus, one or more extension cycles used in a method set forth herein can be done on an apparatus without the need for a detection system which records nucleotide incorporation events, for example, the signals from the incorporated labels attached to nucleotides. A device like an Illumina Cluster Station, or as described in application WO 2008/002502 or U.S. application Ser. No. 12/305,347, the contents of which are incorporated herein by reference in their entirety, is able to pump reagents through a flow cell, and would thus be able to carry out the incremental extension cycles as described herein. If desired a device can be maintained at a set temperature for isothermal extension or temperature can be changed between various steps of an extension protocol if desired.

It is possible that in a given extension process, some nucleic acid fragments might end synthesis prematurely (for example, if they come to a break in the template). To exclude those shorter molecules from full length molecules in a population of fragments, and thus further increase the proportion of the fragments which are full length, it is possible to selectively modify full length molecules to incorporate an element, such as a biotin moiety or other hapten, which can be used for affinity-based selection or another method of selection. For example, a nucleotide having the element can be selectively added to full length nucleic acid molecules during the final cycle of an extension method. Molecules which ended synthesis prematurely would not incorporate this last element, and thus would not be selected in a subsequent affinity-based selection step. Alternatively or additionally, the efficiency of an extension process can be further improved by incorporating a blocking step during synthesis, either in every cycle or selected cycles. Such a blocking step serves to limit the amount of shorter material which can be extended in subsequent cycles by preventing extension of the terminal position of the shortened strand.

Cycles of sequencing using nucleotides having reversible blocking moieties as developed by Illumina and implemented on a Genome Analyzer, take about 15 minutes per cycle for synthesis. This would mean that to synthesize 200 base fragments (which would take 200 cycles of nucleotide incorporation) would take 50 hours of automated sample preparation. Synthesis of longer molecules for paired-end sequencing would take proportionately longer, but are still fully automatable and require no manual input. The fluidic cycle may involve a cycle of incremental extension and a cycle of deblocking to allow extension in the next cycle. The cycle may include further washing steps to help ensure the deblocking reagent and extension reagent do not mix in the flow cell. The steps in each extension cycle may be carried out at the same temperature or at different temperatures. For example, the deblocking and extension may be carried out at different temperatures.

Alternatively or additionally, it is also possible to carry out an extension process using oligonucleotides and a ligase. The oligonucleotides may be of any length, and may include randomised positions wherein all four bases are present at one or more of positions in the oligonucleotide. The oligonucleotides may be any of a variety of lengths including, for example, 2-20 bases in length. A two base oligonucleotide may comprise up to 16 different dinucleotides. A five base oligonucleotide may comprise up to 1024 different pentanucleotides and a 10 base oligonucleotide may comprise up to 1,048,576 decamers. The oligonucleotides may comprise a population of N-mer oligonucleotides including all nucleotide sequences of length N, for example, all N-mer oligonucleotides that can be created by degenerate synthesis using N cycles and all four nucleotides per synthesis cycle. The oligonucleotides may be labelled or unlabelled.

Oligonucleotides used in a method set forth herein may include a blocking moiety to prevent ligation of more than one oligonucleotide to an extending strand per cycle. Alternatively the oligonucleotide may lack a phosphate group on both termini such that the ligation can only occur onto a phosphorylated primer or extension product. The end of a nonphosphorylated oligonucleotide may be activated to subsequent ligation by the addition of a phosphate, or by cleavage of the strand to release an internal phosphate moiety. Suitable mechanisms for ligase based extension cycles are disclosed in U.S. Pat. No. 6,306,597, WO 2006/084132, US 2008/0003571, WO 2007/002890 and US 2007/0026438, the contents of which are incorporated herein by reference in their entirety. A ligation based approach to cycles of incremental extension, such as the embodiments exemplified above, can also be used to get a population of molecules of very uniform length, which could then be used for paired-end sequencing.

As used herein, the term "nucleotide" includes naturally occurring nucleotides and nucleotide analogs. Typically, a nucleotide contains a single 5 carbon sugar moiety, a single nitrogenous base moiety and 1 to three phosphate moieties. In particular embodiments, a nucleotide can include a blocking moiety or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, magnetic labels and the like. One or more of the above moieties can be absent from a nucleotide used in the methods and compositions set forth herein. For example, a nucleotide can lack a label moiety or a blocking moiety or both.

As used herein, the term oligonucleotide includes a polymer of two or more nucleotide subunits. The nucleotide subunits can be naturally occurring nucleotides or nucleotide analogs. The backbone of an oligonucleotide is typically a sugar phosphate backbone but other backbone structures can be used including, but not limited to a protein nucleic acid backbone. An oligonucleotide can be any of a variety of lengths including, but not limited to 3 or more nucleotides, 5 or more nucleotides, 8 or more nucleotides, 10 or more nucleotides, 12 or more nucleotides, 15 or more nucleotides, 20 or more nucleotides, 25 or more nucleotides, 50 or more nucleotides, 75 or more nucleotides, or 100 or more nucleotides.

Incremental extension cycles used in a method set forth herein can be carried out on a solid support. As used herein the term "solid support" includes one or more materials to which nucleic acids can be attached. Examples include, but are not limited to a plate, bead, particle, slide, microtiter plate, well, flowcell, microarray or a plurality of such materials. In embodiments using a plurality of materials, a plurality of different nucleic acids can be attached to a single material such as a single bead or single particle. In particular embodiments, different nucleic acids can be attached to different separable materials. For example, each bead or particle in a plurality of beads or particles can have a single type of nucleic acid attached. It will be understood that multiple species of a single type of nucleic acid can be attached to each bead or particle. Exemplary solid supports are made from plastics such as acrylic, polystyrene and copolymers of styrene and other materials; polypropylene; polyethylene; polybutylene; polyurethane; ceramics; glass, such as modified glass or functionalized glass; paramagnetic materials; thoria sol; metal; optical fiber bundles; carbon graphite; titanium dioxide; latex; polysaccharides; nitrocellulose; resin; silica; silica-based materials such as silicon or modified silicon; or cross-linked dextrans such as Sepharose™; cellulose, and nylon.

Double stranded fragments, such as those synthesized by a method described herein, can be separated from single stranded material for subsequent analysis of the double stranded fragments. For example, double stranded fragments can be separated from single stranded nucleic acids remaining after an extension process, and the double stranded fragments can be sequenced using a desired paired-end sequencing method. Alternatively, synthesized 2nd strands produced by an incremental extension process can be de-hybridized from the target nucleic acids upon which they were synthesized, and the second strands used from there. If desired, conditions can be used to preserve the target nucleic acids allowing the template to be used again in a separate extension process.

The methods described herein allow the assembly of the sequence of a target nucleic acid sample. The target sample may be cleaved into short pieces prior to undergoing cycles of incremental extension to produce a population of nucleic acid fragments including different portions of the target nucleic acid. The cleaved target sample can provide a plurality of templates suitable for the controlled growth of fragments complementary to the templates. Methods used to cleave target nucleic acids isolated from a biological source, for example, genomic DNA, into shorter pieces include sonication, forcing through a nozzle that forms tiny droplets (nebulisation), chemical cleavage, heat and radiation. These methods typically result in random fragments (e.g. minimal base-composition bias) but wide length distributions.

Templates for use in a method set forth herein may be copied using a population of random primers that anneal to random priming sites, or the templates can have a universal adapter to which a common universal primer will anneal. The templates may be modified so that the ends of the templates carry universal sequences such that several different templates can be amplified using the same universal primers. Examples of methods of attaching universal ends to a collection of target fragments can be found in US 2007/0128624, the contents of which are incorporated herein by reference in their entirety. A universal primer is a primer sequence capable of hybridising to a universal adapter. The attachment of the adapter allows hybridisation of a universal primer to each template carrying the adapter.

Alternatively a pool of selected priming sequences might be used in order to select out or "enrich" certain portions of the target sample of interest. Reducing the complexity of a nucleic acid sample in a reproducible manner by enriching for specific nucleic acid target sequences in the population serves to limit the amount of sequencing required to analyse the sample. For example a pool of two or more specified primers may be synthesised, hybridised to the templates and used as a starting point for the incremental extension cycles. Any number of primer sequences may be selected, depending on the size and complexity of the sample to be analysed. For example a pool of 1000 primers may be synthesised and used to hybridise at regions across a sequence of 1 megabase. Alternatively, primers designed to hybridise close to the vicinity of a genomic marker can be used. For selecting larger regions of sample, pools of at least 10000 or at least 100000 primers may be used.

Templates for use in a method set forth herein may be attached directly to a solid support. Alternatively, the templates may be attached to the support via hybridisation to an immobilised primer. A plurality of primers may have a universal sequence complementary to an adapter that is present on several different templates in a population of target nucleic acids. Alternatively, individual primers in the plurality of primers can each have a different sequence capable of hybridising directly to a different template in the target sample. A primer may be attached to a support by a cleavable moiety to allow removal of an extension product, such as a population of fragments produced by an incremental extension process, from the support. Suitable cleavable moieties are described at length in applications US 2009/0118128 and WO2007/010251, the contents of which are incorporated herein by reference in their entirety. For example, the primers may be attached to the surface through a linkage comprising a diol moiety, or may include one or more nucleotides which can be transformed into an abasic site, such as uracil or 8-oxo-guanine. Treatment with UDG and an endonuclease (e.g the USER mix from New England Biolabs, part number M5505) selectively cleaves a primer containing a uracil base. Treatment with FPG glycosylase (New England Biolabs, part number M0240) cleaves a primer containing an 8-oxo-guanine base.

Nucleic acid fragments produced by incremental cycles of extension may be treated to attach a universal adapter sequence. For example, in embodiments wherein the fragments have a first universal adapter sequence, a second universal adapter sequence can be added after incremental cycles of extension are carried out. The adapter may be ligated onto the extended end of the fragments such that the fragments have universal regions at both ends. The known ends can serve as sites for hybridisation of primers in future amplification and or sequencing steps. The treatment to attach a universal adapter sequence may be carried out on a solid support to which the fragments are attached.

A population of fragments whose length is correlated with the number of extension cycles can be sequenced such that a sequencing read is obtained from both ends of each fragment. Each fragment in the population can generate a first and second read separated by defined length. From these three pieces of information, the sequence of the target nucleic acid can be determined.

Sequencing reads may be obtained on a solid support. In particular embodiments, a population of nucleic acids can be produced by incremental extension cycles on a first support followed by sequencing on a second support after removal of the population from the first support. The population may be sequenced as single molecules, or the population may be amplified, for example via bridge amplification or in an emulsion. The second solid support may carry the population of nucleic acids as an array of single molecules which are capable of individual resolution. Exemplary single molecule arrays are described in US 2005/0042649 and US 2004/0106110, the contents of which are incorporated herein by reference in their entirety. Alternatively the molecules may be amplified, either on the second solid support, on a further support such as a population of beads or particles, or in solution. As such an ensemble or population of nucleic acid molecules is produced and can be used in the methods set forth herein. Examples of suitable amplification methods to produce clustered arrays via bridge amplification, or using emulsion PCR are detailed in US 2005/0100900 and U.S. Pat. No. 7,323,305 respectively, the contents of which are incorporated herein by reference in their entirety.

Sequencing reads of the first and second ends of nucleic acid fragments can either be on the same strand, or on complementary strands, of a double-stranded polynucleotide template, which are referred to herein respectively as first and second template strands. The population of fragments can be in the form of a library of 3' and 5' modified nucleic acids suitable for paired end sequencing as the 5' and 3' ends of each fragment contain known sequences, whereas the internal sequences between the known ends are unknown. Typically, the known sequence on one or both ends of each fragment in a population of fragments is the same, although the 3' ends and 5' ends might be different from each other. In a population of nucleic acid fragments, the region between the two known ends is typically of different sequence composition, when comparing the different individual members of the population. Furthermore it will be understood that a population of fragments can include several subpopulations, wherein the fragments in each subpopulation have the same known sequence ends but the known sequences at the ends of the fragments in the different subpopulations differ from each other.

The term "target nucleic acid" is used herein to refer to the primary nucleic acid sample whose sequence is to be determined. The target nucleic acid may be cleaved into shorter pieces to form a plurality of templates, which can be used to produce a population of nucleic acid fragments. The population of nucleic acid fragments may be generated by making complementary copies of the plurality of templates. Alternatively the target nucleic acid may be used directly without being cleaved into a plurality of templates.

The term "target nucleic acid sequence" is used to refer to the sequence of the target nucleic acid from a primary nucleic acid sample. The target nucleic acid sequence can be assembled from the combined knowledge of the first and second sequencing reads and the defined length of the fragments for the individual members of the population of nucleic acid fragments.

Sequencing may be performed on an array of amplified fragments according to the invention. The target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample that has been randomly fragmented. The targets can also be obtained from a primary RNA sample by reverse transcription into cDNA.

As used herein, the terms "polynucleotide", "oligonucleotide" or "nucleic acid" can refer to deoxyribonucleic acid (DNA), ribonucleic acid (RNA) or analogs of either DNA or RNA made, for example, from nucleotide analogs. The terms "polynucleotide", "oligonucleotide" or "nucleic acid" are applicable to single stranded (such as sense or antisense) and double stranded molecules. The terms "polynucleotide", "oligonucleotide" or "nucleic acid" as used herein also encompass cDNA, that is complementary or copy DNA produced from an RNA template, for example by the action of reverse transcriptase.

The nucleic acid molecules in a primary nucleic acid sample may originate in double-stranded DNA (dsDNA) form (e.g. genomic DNA fragments, PCR and amplification products and the like) or may have originated in single-stranded form, as DNA or RNA, and been converted to dsDNA form. A target nucleic acid used in a method set forth herein may be the whole of, or a portion of the nucleic acid molecules in a primary nucleic acid sample or derived from a primary nucleic acid sample. By way of example, mRNA molecules may be copied into double-stranded cDNAs suitable for use in a method of the invention using standard techniques well known in the art. Thus the cDNA molecules form target nucleic acids that are derived from the primary sample of mRNA molecules. Similarly a target nucleic acid may contain a subset of genomic sequence from a primary nucleic acid sample which is a whole genome. The precise sequence of the primary nucleic acid sample molecules useful in the invention may be known or unknown.

In a particular embodiment, the primary nucleic acid sample molecules are DNA molecules. A population of the primary nucleic acid sample molecules can represent the entire genetic complement of an organism or a portion thereof. For example, the population can include at least 50%, 75%, 90%, 95%, 98%, or 99% of the genetic complement of an organism. The population can include genomic DNA molecules which include both intron and exon sequences (coding sequence), as well as non-coding regulatory sequences such as promoter and enhancer sequences. In an embodiment wherein genomic DNA molecules are used, genome-wide analysis or analysis of the entire genome may be achieved. It is, however, envisaged that particular sub-sets of polynucleotide sequences or genomic DNA could also be used, such as, for example, particular chromosomes obtained by known chromosome isolation methods or coding sequences derived from a cDNA sample. The subsets of the genome may be selected, for example using hybridisation with pools of oligonucleotides, for example as described in co-pending applications WO 07/057652 and US 2007/0141604, the contents of which are incorporated herein by reference in their entirety. The sequence of primary nucleic acid sample molecules can be known but need not be known in order to function as a target nucleic acid sample in the methods set forth herein. Primary nucleic acid sample molecules can be human genomic DNA molecules. Nucleic acids in a sample may be treated chemically or enzymatically, either prior to, or subsequent to any random fragmentation processes, and prior to or subsequent to the ligation of any adaptor sequences.

Random fragmentation refers to the fragmentation of a polynucleotide molecule in a non-ordered fashion, for example, by enzymatic, chemical or mechanical means. Such fragmentation methods are known in the art and utilise standard methods (Sambrook and Russell, *Molecular Cloning, A Laboratory Manual*, third edition, which is incorporated herein by reference). In some embodiments, the random fragmentation methods do not include methods in which smaller fragments are amplified from a larger piece of nucleic acid sequence that remains in intact. However, in other embodiments shorter nucleic acid strands can be obtained by amplifying smaller regions of a larger nucleic acid sequence. Moreover, random fragmentation is typically designed to produce fragments irrespective of the sequence identity or position of nucleotides comprising and/or surrounding a break in the larger nucleic acid sequence. In the application of methods described herein, fragmentation may be, for example, in the range 50-10000 bases. Fragmentation of polynucleotide molecules by mechanical means (nebulization, sonication and Hydroshear for example) results in fragments with a heterogeneous mix of blunt and 3'- and 5'-overhanging ends. It may therefore be desirable to repair the fragment ends using methods or kits (such as the Lucigen DNA terminator End Repair Kit) known in the art to generate ends that are useful for insertion, for example, into blunt sites of cloning vectors, or to undergo adapter ligation. In a particular embodiment, the fragment ends of the population of nucleic acids are blunt ended. One method of the invention involves repairing the fragment ends with nucleotide triphosphates and a nucleic acid polymerase. The nucleotide triphosphates may contain a labelling modification, for example biotin or similar protein binding ligand, that allows selection of the end repaired fragments. The polymerase may be Klenow DNA polymerase, or similar nucleic acid polymerase, that may have exonuclease activity in order to remove any 3' overhanging ends. The reaction may be carried out with all four nucleotides, of which 0-4 may carry labelling modifications.

Fragmentation of a primary nucleic acid sample may also be achieved using randomised amplification, for example with randomised primers. Randomised primers are members of a population of primers, the population being degenerate with respect to having 2 or more different nucleotide species at one or more positions along a given length of primer sequence. For example, a population of primers can include individual primers having one of four different nucleotide species at every position along a given length such that the population as a whole includes every possible sequence of that length. In some embodiments randomized primers can be members of a population in which a first region of the primers is randomized and a second region is common to all of the primers in the population. Random amplification may also be obtained by using low stringency conditions that result in mis-priming of a particular sequence, or by using primers containing universal bases that can hybridise against more than one of the nucleobases in a template strand.

Whilst the primary sample remains intact in randomised amplification, this process is described as "fragmentation" for the purposes of this application, as a collection of shorter pieces of the original sample are obtained. The primers used in randomized amplification may carry a ligand allowing for their later selection. Such a ligand may be biotin, dinitrophenol, fluorescein or any other molecule that can be attached to a short oligonucleotide sequence. Selection can utilize a known receptor that can be used to bind to the ligand. Alternatively or additionally, selection can utilize specific detection of the ligand in combination with a separation technique such as chromatography. Each of the primers may carry a ligand, or a subset of the primers may carry a ligand, with the remainder being unlabelled. The randomised primers may be used to amplify any sequence of interest. Conditions for random primer amplification of target sequences using a nucleic acid polymerase and four nucleotide triphosphates are well known in the art, and kits for random primer amplification are available. If the method is performed using primer amplification rather than mechanical fragmentation of the primary sample, then the products will automatically be blunt ended, so there is no requirement for the enzymatic polishing of fragments.

In a particular embodiment, in order to efficiently ligate a universal adapter, cleaved target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes can be utilised to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both vector and target such that there is a bias towards formation of the combined ligated adaptor-target sequences.

A population of linear double stranded template nucleic acid fragments can be provided for use in a method of the invention. The length of the template which is copied using the incremental extension cycles may be 50 bases or more. The number of incremental extension cycles may be 100, 200, 300, 400, 500, 600, 700, 800, 900 or 1000 or more. In cases using ligation of oligonucleotides, the number of cycles multiplied by the length of the oligonucleotide may be 100, 200, 300, 400, 500, 600, 700, 800, 900 or 1000 or more. The length of the template may be longer than the fragments generated by extending a primer complementary to the template. The protocol of incremental extension cycles can be independent of the length of the template fragments.

If the fragments generated by a particular technique do not have known ends, they may be treated by the ligation of adapters using known methods, for example as described in co-pending applications WO 07/052006 and US 2007/0128624, the contents of which are incorporated herein by reference in their entirety. Such treatment can be useful in preparing the fragments for sequencing as set forth herein. The ends of the linear fragments can be ligated to known adapter sequences. The known adapter sequences can be universal adapter sequences located on the ends of each fragment to allow universal amplification, whereby a single pair of primers is used to amplify a plurality of different target sequences by hybridizing to the common adapter sequences that flank the different target sequences. The adapters may contain a region of double stranded sequence to enable ligation to fragment nucleic acids produced by cycles of extension, and may further contain a region of single stranded non-complementary sequence. These adapters may be termed mismatched adapters. Mismatched adaptors for use in the invention can be formed by annealing two partially complementary polynucleotide strands so as to provide, when the two strands are annealed, at least one double-stranded region and at least one unmatched region. The adapters may also contain a single overhanging base complementary to the overhanging base on the target fragments.

Adaptors for use in the invention will generally include a double-stranded region forming the "ligatable" end of the adaptor, i.e., the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor is preferably phosphorylated for example to enable phosphodiester linkage to a 3' hydroxyl group on the target polynucleotide.

It is generally advantageous, where it is desired for complex libraries of templates to be amplified, for example by PCR or isothermal amplification (e.g. whole genome amplification), either in solution or on a solid support, to include universal regions at their 5' and 3' ends, which are common to all template molecules in the library. Additionally, the presence of a common unique sequence at one end only of each template in the library can provide a binding site for a sequencing primer, enabling one strand of each template in the amplified form of the library to be sequenced in a single sequencing reaction using a single type of sequencing primer. The method of the invention may also be applied to the preparation of libraries which are amplified in vivo, such as for example bacterial cDNA libraries and the like.

The precise nucleotide sequences of the universal regions of the template molecules in the library can be selected by the user. In particular embodiments, the universal sequences must at least include "primer-binding" sequences which enable specific annealing of primers when the templates are in use in a solid-phase amplification reaction. The primer-binding sequences are thus determined by the sequence of the primers to be used for solid-phase amplification. The sequence of these primers in turn is advantageously selected to avoid or minimise binding of the primers to the target portions of the templates within the library under conditions used for the amplification reaction, but is otherwise not particularly limited. By way of example, if the target portions of the templates are derived from human genomic DNA, then the sequences of the primers to be used in solid phase amplification can be selected to minimise non-specific binding to any human genomic sequence.

The conditions encountered during the annealing steps of an amplification reaction will be generally known to one skilled in the art, although the precise annealing conditions will vary from reaction to reaction (see Sambrook et al., 2001, *Molecular Cloning, A Laboratory Manual*, 3rd Ed, Cold Spring Harbor Laboratory Press, Cold Spring Harbor Laboratory Press, NY; *Current Protocols*, eds Ausubel et al.). Typically such conditions may include, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

The precise nucleotide sequence of adaptors used in various embodiments of the invention may be selected by the user such that the desired sequence elements are ultimately included in the common sequences of the library of templates derived from the adaptors, for example to provide binding sites for particular sets of universal amplification primers and/or sequencing primers. Additional sequence elements may be included, for example to provide binding sites for sequencing primers which may ultimately be used in sequencing of template molecules in the library, or products derived from amplification of the template library, for example on a solid support. The adaptors may further include "tag" sequences, which can be used to tag or mark template molecules derived from a particular source. The general features and use of such tag sequences is described in applicant's pending application published as WO 05/068656 and US 2008/0051294.

Although any of a variety of nucleotide sequences can be used as a first or second adaptor, in some embodiments the sequences of the individual strands in the unmatched region should be such that neither individual strand exhibits any internal self-complementarity which could lead to self-annealing or formation of hairpin structures, etc. under standard annealing conditions. Self-annealing of a strand in the unmatched region is to be avoided in particular embodiments as it may prevent or reduce specific binding of an amplification primer to this strand.

Use of the Population of Nucleic Acid Fragments

A population of nucleic acid fragments may be used in methods of sequencing, either as an array of single molecules or as an array of features, wherein each feature contains an ensemble or population of molecules having a common sequence. An array of single molecules can be made and used as described in WO 00/06770 US 2005/

0042649 and US 2004/0106110 (incorporated herein by reference). Nucleic acids may be amplified to form an array of features prior to sequencing, for example, either on beads, in an emulsion or on a planar array. Exemplary amplification methods are described in WO 04/069849 and U.S. Pat. No. 7,323,305 (incorporated herein by reference).

One suitable format for sequence analysis of a population of nucleic acid fragments is the provision of a plurality of polynucleotide duplexes immobilised on a solid support in the form of amplified clusters as described in WO 98/44151, US 2005/0100900, U.S. Pat. No. 7,115,400 or WO 00/018957, whose contents are incorporated herein by reference. Each of the duplexes within a particular cluster typically has the same double-stranded target region to be sequenced. The duplexes are each formed from complementary first and second template strands which are linked to the solid support at or near to their 5' ends. Typically, the polynucleotide duplexes will be provided in the form of a clustered array. Amplification of the array may be carried out using thermocycling, or isothermally, using changes of reagents to denature the hybridised strands.

WO 07/010252, WO 07/091077, US 2009/0088327 and WO 08/041002 which are incorporated herein by reference in their entirety, describe various methods of reading both the first and second strands from each cluster. For example, one of the strands of the cluster may be removed from the surface in order to sequence a region of the remaining strand. The remaining strand can then be copied back into a duplex, and removed from the surface to leave the copied strand, which can then be sequenced. It is thus possible to sequence both ends of each nucleic acid cluster on the array. The length of each strand in the cluster is defined by the length of the fragments produced by the incremental extension cycles.

When referring to immobilisation or attachment of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications utilizing nucleic acid amplification and/or sequencing.

Certain embodiments of the invention may make use of solid supports comprised of an inert substrate or matrix (e.g. glass slides, polymer beads etc) which is been "functionalised", for example by application of a layer or coating of an intermediate material comprising reactive groups which permit covalent attachment to biomolecules, such as polynucleotides or oligonucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

After amplification to produce nucleic acid clusters on a solid support according to some embodiments of the invention, the clusters are in the form of hybridised duplexes. In order to hybridise a primer for sequencing, the clusters, or colonies, may be treated to remove one of the strands from the surface. If the molecules are immobilised such that one of the two immobilised ends can be cleaved from the surface, upon such cleavage the resulting double stranded DNA, which is now immobilised at only one end of the duplex, can be made single stranded using heat or chemical denaturing conditions to give a single stranded molecule containing a primer hybridisation site. The process of removing all or a portion of one immobilised strand in a "bridged" double-stranded nucleic acid structure may be referred to herein as "linearization". The single stranded molecule can be sequenced using a first sequencing primer which is capable of hybridisation to the remaining single stranded template.

Either the first or second strand of the polynucleotide duplexes in nucleic acid clusters may include a cleavage site for linearization of the duplex strands. The cleavage site is a site which allows controlled cleavage of the first or second template strand by chemical, enzymatic or photochemical means. After cleavage of the cleavage site, the double stranded polynucleotide is then only immobilised through one end. The polynucleotide can then be denatured to leave a single stranded polynucleotide immobilised at the 5'-end. A first sequencing primer can then be hybridised to a single-stranded region of the template and used as the primer for a sequencing reaction, after which it may be removed from the template, and a second sequencing primer hybridised and used for sequencing of a different region of the single stranded template.

Any suitable enzymatic, chemical or photochemical cleavage reaction may be used to cleave nucleic acids. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulphide linkage with a reducing agent (e.g. TCEP), in which case the cleavage site may include an appropriate disulphide linkage; chemical cleavage of a diol linkage with periodate, in which case the cleavage site may include a diol linkage; generation of an abasic site and subsequent hydrolysis, etc.

In one embodiment cleavage may occur at a cleavage site in one or both strands of a template polynucleotide duplex which comprises one or more or any combination of non-natural nucleotides, ribonucleotides or a non-nucleotide chemical modifications. Suitable cleavage techniques for use in the method of the invention are described, for example, in WO 07/010251 and US 2009/0118128, which are incorporated herein by reference.

Once cleaved, the polynucleotides can then be treated in such a way to allow primer hybridisation. This can be performed either by heating the amplified clusters to denature the duplexes, followed by cooling in the presence of the first sequencing primer, by a chemical treatment such as sodium hydroxide to denature the duplexes or by a treatment to cleave one or both of the strands of the duplex polynucleotide.

Each polynucleotide sequence on an array may contain the same universal primer recognition regions to allow the same primers to be used to sequence every cluster. A first sequencing primer can then be hybridised to the first template strand and a sequencing reaction carried out via successive incorporation of nucleotides to the first sequencing primer, resulting in determination of the sequence of a first region of the target polynucleotide.

Hybridisation of a sequencing primer to a template strand is achieved by contacting the primer and template strand under conditions which promote annealing of primer to template. Such conditions will generally be well known to those skilled in the art of molecular biology.

When a first sequencing reaction is complete, the extended first sequencing primer may be removed from the surface. This can be achieved by heating, or chemical denaturation. If an adaptor region is present in the clusters between the two end regions, a second sequencing primer can then be hybridised to the adaptor region of the template and a sequencing reaction can proceed via successive addition of nucleotides to the second sequencing primer, resulting in determination of the sequence of a second region of the target polynucleotide. Alternatively the strand may be inverted on the surface to allow sequencing of the other end of the strand.

Sequencing can be carried out using any suitable "sequencing-by-synthesis" technique, wherein nucleotides or oligonucleotides are added successively to a free hydroxyl group, typically provided by annealing of a sequencing primer, resulting in synthesis of a polynucleotide chain. In a particular embodiment, the nature of the nucleotide added is determined after each addition.

One particular sequencing method which can be used in the methods of the invention relies on the use of modified nucleotides having blocking moieties that can act as reversible chain terminators. Exemplary nucleotides for use in the invention are described in WO 04/018497, U.S. Pat. Nos. 7,541,444 and 7,057,026, each of which is incorporated herein by reference. Once the modified nucleotide has been incorporated into the growing polynucleotide chain complementary to the region of the template being sequenced there is no free 3'—OH group available to direct further sequence extension and therefore the polymerase can not add further nucleotides. Once the nature of the base incorporated into the growing chain has been detected or determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, which facilitates discrimination between the bases added at each incorporation step. Alternatively, a separate reaction may be carried out containing each of the modified nucleotides, which are added separately.

The modified nucleotides that are used in a method set forth herein may carry a label to facilitate their detection.

In a particular embodiment, the label is a fluorescent label. Each nucleotide type may carry a different fluorescent label. Fluorescent labels suitable for use in the current invention are described in WO 2007/135368, which is incorporated herein by reference. However the detectable label need not be a fluorescent label. Any label can be used which allows the detection of the incorporation of the nucleotide into the DNA sequence.

One method for detecting fluorescent labels, for example on nucleotides, comprises using laser light of a wavelength specific for the label, or the use of other suitable sources of illumination. The fluorescence from a label may be detected by a CCD camera or other suitable detection means. Imaging systems suitable for determining the fluorescent signal from incorporated nucleotides are described, for example, in WO 2007/123744 and U.S. Pat. No. 7,329,860, each of which is incorporated herein by reference.

The methods of the invention are not limited to use of the sequencing method outlined above, but can be used in conjunction with essentially any sequencing methodology including, but not limited to, methods which rely on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods, for example as described in U.S. Pat. No. 6,306,597 or WO 2006/084132, the content of which are incorporated herein by reference in their entirety.

Solid supports can be manufactured from materials such as glass, ceramics, silica and silicon. Supports with a gold surface may also be used. The supports may comprise a flat (planar) surface, or at least a structure in which the polynucleotides to be interrogated are in approximately the same plane. Alternatively, the solid support can be non-planar, e.g., a microbead. Any suitable size may be used. For example, the supports might be on the order of 1-10 cm in each direction. The solid support may comprise a flow cell, in order to aid the transfer of reagents to the solid support.

Solid supports may be coated with a layer of primer sequences via a grafting reaction. For the grafting reaction to proceed, a mixture of the amplification primers can be applied to a (suitably functionalised) solid support under conditions which permit reaction between the primer and the support. The result of the grafting reaction can be a substantially even distribution of the primers over the solid support.

In certain embodiments a population of nucleic acid fragments to be amplified, or a plurality of templates which undergo incremental extension cycles, may be grafted onto a solid support together with amplification primers in a single grafting reaction. Amplification may then proceed using the immobilised template and primers in a reaction analogous to that described in WO 00/18957 or U.S. Pat. No. 7,115,400, each of which is incorporated herein by reference. The first step in such a reaction can be hybridisation between surface-bound templates and surface-bound amplification primers.

For embodiments wherein a mixture of primers only is grafted onto a solid support and a template to be amplified is present in free solution, the amplification reaction may proceed substantially as described in WO 98/44151 or US 2005/0100900, which are incorporated herein by reference. Briefly, following attachment of the primers the solid support is contacted with the template to be amplified under conditions which permit hybridisation between the template and the immobilised primers. The template may be added in free solution under suitable hybridisation conditions, which will be apparent to the skilled reader. Typically hybridisation conditions are, for example, 5×SSC at 40° C., following an initial denaturation step. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support. Further rounds of extension, denaturation and hybridisation to immobilised primer lead to the formation of clusters or colonies of template molecules bound to the solid support.

The sequencing methods of the invention are not limited to sequencing of templates produced by an amplification reaction. The method may be applied to sequencing of any template immobilised on a support by any other means amenable to repeated cycles of hybridisation and sequencing.

The two sequencing reads generated by the methods described herein may come from two regions of a target nucleic acid separated by a few hundred basepairs, or may come from two regions of a target separated by many thousands of basepairs, the separation depending on the number of incremental extension cycles carried out when the fragments are produced. The size of the fragments to be sequenced can be accurately controlled by preparing the fragments as described herein, which greatly aids in the accuracy of aligning the reads to build the original target sequence. The target can be sequenced by determining the relative locations of the first end sequences and the second end sequences in the sequence of the target nucleic acid based on the defined length of the individual nucleic acid fragments. The target sequence can be determined if the relative locations of the first end and second end sequences are fixed based on the defined length of the individual nucleic acid fragments. The defined length of the fragments is fixed by the number of incremental extension cycles carried out, but may, for example be between 200-1000 cycles of addition of a single nucleotide. Each fragment will be known to within a few nucleotides, for example the majority of the fragments in the population of fragments may be 195-205 bases in size, or 990-1010 in size.

While the foregoing invention has been described in some detail for purposes of clarity and understanding, it will be clear to one skilled in the art from a reading of this disclosure that various changes in form and detail can be made without departing from the true scope of the invention. For example, all the techniques described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method of preparing a library of nucleic acid fragments for sequence analysis, comprising:
   (a) cleaving a target nucleic acid to produce a plurality of double-stranded cleavage products, wherein the target nucleic acid comprises human genomic DNA;
   (b) ligating a first universal adapter to the double-stranded cleavage products to form a plurality of double-stranded templates having known ends, wherein the first universal adapter comprises a region of double-stranded sequence for ligation to the double-stranded cleavage products, and a first universal adapter sequence;
   (c) denaturing the double-stranded templates to produce a plurality of single-stranded templates comprising the first universal adapter sequence;
   (d) annealing the single-stranded templates to a population of complementary primer nucleic acids attached to a solid support;
   (e) performing a defined number of at least 50 incremental extension cycles, each extension cycle comprising:
      (i) extending each of the primer nucleic acids by incorporating an unlabeled nucleotide complementary to the annealed template and comprising a reversible blocking moiety; and
      (ii) contacting the incorporated nucleotide with a deblocking agent to remove the blocking moiety;
   thereby producing a population of extended primers comprising different portions of the target nucleic acid, wherein the individual extended primers in the population comprise a defined length that is correlated with the number of incremental extension cycles;
   (f) subjecting the annealed templates to denaturing conditions to remove the templates from the solid support; and
   (g) ligating a second universal adapter sequence to the 3' ends of the extended primers to produce a population of immobilized nucleic acid fragments having universal adapter sequences at both ends;
   thereby preparing a library of nucleic acid fragments for sequence analysis.

2. The method of claim 1, wherein individual cycles in the incremental extension cycles comprise a wash step to remove an unreacted reagent.

3. The method according to claim 1, wherein the primer nucleic acids attached to the solid support comprise a cleavable linkage.

4. The method of claim 1, further comprising:
   (h) removing the nucleic acid fragments having a defined length and universal adapter sequences at both ends from the solid support.

5. The method of claim 1, wherein the defined length of the immobilized nucleic acid fragments is such that at least 50% of the immobilized nucleic acid fragments have a defined length that varies by less than 5 nucleotides.

6. The method of claim 1 wherein the defined length is between 200-1000 bases.

7. The method of claim 1, wherein the number of incremental extension cycles performed in step (e) is between 100-1000 cycles.

8. The method of claim 1, wherein the first universal adapter comprises a region of single-stranded sequence comprising the first universal adapter sequence.

9. A method of preparing a library of nucleic acid fragments for sequence analysis, comprising:
   (a) cleaving a target nucleic acid to produce a plurality of double-stranded cleavage products, wherein the target nucleic acid comprises human genomic DNA;
   (b) ligating a single-stranded first universal adapter to the 3' ends of the double-stranded cleavage products to form a plurality of double-stranded templates having known 3' ends, wherein the first universal adapter comprises a first universal adapter sequence;
   (c) denaturing the double-stranded templates to produce a plurality of single-stranded templates comprising the first universal adapter sequence;
   (d) annealing the single-stranded templates to a population of complementary primer nucleic acids attached to a solid support;
   (e) performing a defined number of at least 50 incremental extension cycles, each extension cycle comprising:
      (i) extending each of the primer nucleic acids by incorporating an unlabeled nucleotide complementary to the annealed template and comprising a reversible blocking moiety; and
      (ii) contacting the incorporated nucleotide with a deblocking agent to remove the blocking moiety;
   thereby producing a population of extended primers comprising different portions of the target nucleic acid, wherein the individual extended primers in the population comprise a defined length that is correlated with the number of incremental extension cycles;

(f) subjecting the annealed templates to denaturing conditions to remove the templates from the solid support; and (g) ligating a second universal adapter sequence to the 3' ends of the extended primers to produce a population of immobilized nucleic acid fragments having universal adapter sequences at both ends;

thereby preparing a library of nucleic acid fragments for sequence analysis.

10. The method of claim 9, wherein individual cycles in the incremental extension cycles comprise a wash step to remove an unreacted reagent.

11. The method of claim 9, wherein the primer nucleic acids attached to the solid support comprise a cleavable linkage.

12. The method of claim 9, further comprising:

(h) removing the nucleic acid fragments having a defined length and universal adapter sequences at both ends from the solid support.

13. The method of claim 9, wherein the defined length of the immobilized nucleic acid fragments is such that at least 50% of the immobilized nucleic acid fragments have a defined length that varies by less than 5 nucleotides.

14. The method of claim 9, wherein the defined length is between 200-1000 bases.

15. The method of claim 9, wherein the number of incremental extension cycles is between 100-1000 cycles.

* * * * *